United States Patent [19]

Shoesmith

[11] Patent Number: Plant 5,944

[45] Date of Patent: Apr. 14, 1987

[54] CHRYSANTHEMUM PLANT NAMED SEMINOLE

[75] Inventor: May V. Shoesmith, Westfield, England

[73] Assignee: Ball Pan Am Plant Company, Parrish, Fla.

[21] Appl. No.: 746,889

[22] Filed: Jun. 20, 1985

[51] Int. Cl.[4] ..... A01H 5/00
[52] U.S. Cl. ..... Plt./74
[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Seminole having flat capitulum form and quilled daisy type; bright lavender color when finished under cool temperatures; diameter across face of the flowers of 0.75" to 2"; uniform eight week flowering response when grown photoperiodically and natural flowering season of September 26–October 9; height 6" to 8' above the edge of a 4" pot when grown photoperiodically, and 1' to 2' when grown outdoors, and a compact cushion habit when grown outdoors.

1 Drawing Figure

The present invention comprises a new and distinct cultivar of *Chrysanthemum morifolium,* Ramat., hereinafter referred to by the cultivar name Seminole.

Seminole is a product of a planned breeding program which had the objective of creating new garden type Chrysanthemum cultivars with novel flower types, compact habits, and early flowering.

Seminole was originated from a hybridization made by May Victoria Shoesmith in a controlled breeding program in Westfield, Woking, England in 1979. The male and female parents are unknown at this time.

Seminole was discovered and selected as one flowering plant within the progeny of the stated parentage by or under the supervision of May Victoria Shoesmith in November, 1980 in a controlled environment in West Chicago, Ill., and given the code #FG-80-2021-PS.

The first act of asexual reproduction of Seminole was accomplished when vegetative cuttings were taken from the initial selection in February of 1981 in a controlled environment in West Chicago, Ill. by a technician working under formulations established and supervised by May Victoria Shoesmith. Horticultural examination of selected units initiated in February of 1981 has demonstrated that the combination of characteristics as herein disclosed for Seminole are firmly fixed and are retained through successive generations of asexual reproduction.

Seminole has not been observed under all possible environmental conditions. The phenotype may vary significantly with variations in environment such as temperature, light intensity and day length. The following observations, measurements and comparisons describe plants grown in West Chicago, Ill. and Bradenton, Fla. under greenhouse and field conditions which approximate those generally used in commercial practice.

The following traits have been repeatedly observed and are determined to be basic characteristics of Seminole which in combination distinguish this Chrysanthemum as a new and distinct cultivar:

(1) Flat capitulum form.

(2) Quilled daisy type.

(3) Bright lavender color when finished cool; flower color is a lighter shade of lavender at high temperatures.

(4) Diameter across the face of the flower is 0.75" to 2".

(5) Can be grown as a garden variety or under photoperiodic control.

(6) Uniform 8 week flowering response using photoperiodic control; natural flowering date is midseason between September 26 and October 9.

(7) Height is 6" to 8" above the edge of a 4" pot when grown photoperiodically, and 1' to 2' in the garden. Height is dependent on the time of bud initiation and temperature.

(8) Compact cushion habit when grown in the garden.

Of the many commercial cultivars known to the present inventor, the most similar in comparison to Seminole is Quaker. In comparison to Quaker, Seminole has a more quilled ray floret, lavender flower color, a more compact habit, and is one week later. The flower type is similar to those same characteristics of Quaker.

The accompanying photographic drawing shows typical inflorescence and foliage characteristics of Seminole. The photograph is in black and white except for two flowers which represent the true flower colors of Seminole.

In the following description, color references are made to The Royal Horticultural Society Colour Chart. The color values were determined at approximately 12:00 noon on May 5, 1985 under inflorescent light at Bradenton, Fla.

Classification:

*Botanical.*—*Chrysanthemum morifolium,* Ramat., cv Seminole.

*Commercial.*—Garden and greenhouse mum.

I. INFLORESCENCE

A. Capitulum:

*Form.*—Flat.

*Type.*—Quilled single.

*Diameter Across Face.*—0.75" to 2".

B. Corolla of ray florets:

*Color (general tonality from a distance of three meters).*—Lavender.

*Color (upper surface).*—77C; spoon tip, 77A.

*Color (under surface).*—77B.

C. Corolla of disc florets:
*Color (mature).*—Yellow.
*Color (immature).*—Greenish yellow.

D. Reproductive organs:
*Androecium.*—Present in disc florets only; insignificant.
*Gynoecium.*—One per both ray and disc floret.

II. PLANT

A. General appearance:
*Height.*—6″ to 8″ above the edge of a 4″ pot when grown as a garden variety.

B. Foliage:
*Color (upper surface).*—147A.
*Color (under surface).*—147B.

*Shape.*—Deeply lobed, margin repand.

I claim:

1. A new and distinct cultivar of Chrysanthemum plant named Seminole, as described and illustrated, and particularly characterized by its flat capitulum form and quilled daisy type; bright lavender color when finished under cool temperatures; diameter across face of the flowers of 0.75″ to 2″; uniform eight week flowering response when grown photoperiodically and natural flowering season of September 26–October 9; height 6″ to 8″ above the edge of a 4″ pot when grown photoperiodically, and 1′ to 2′ when grown outdoors, and a compact cushion habit when grown outdoors.

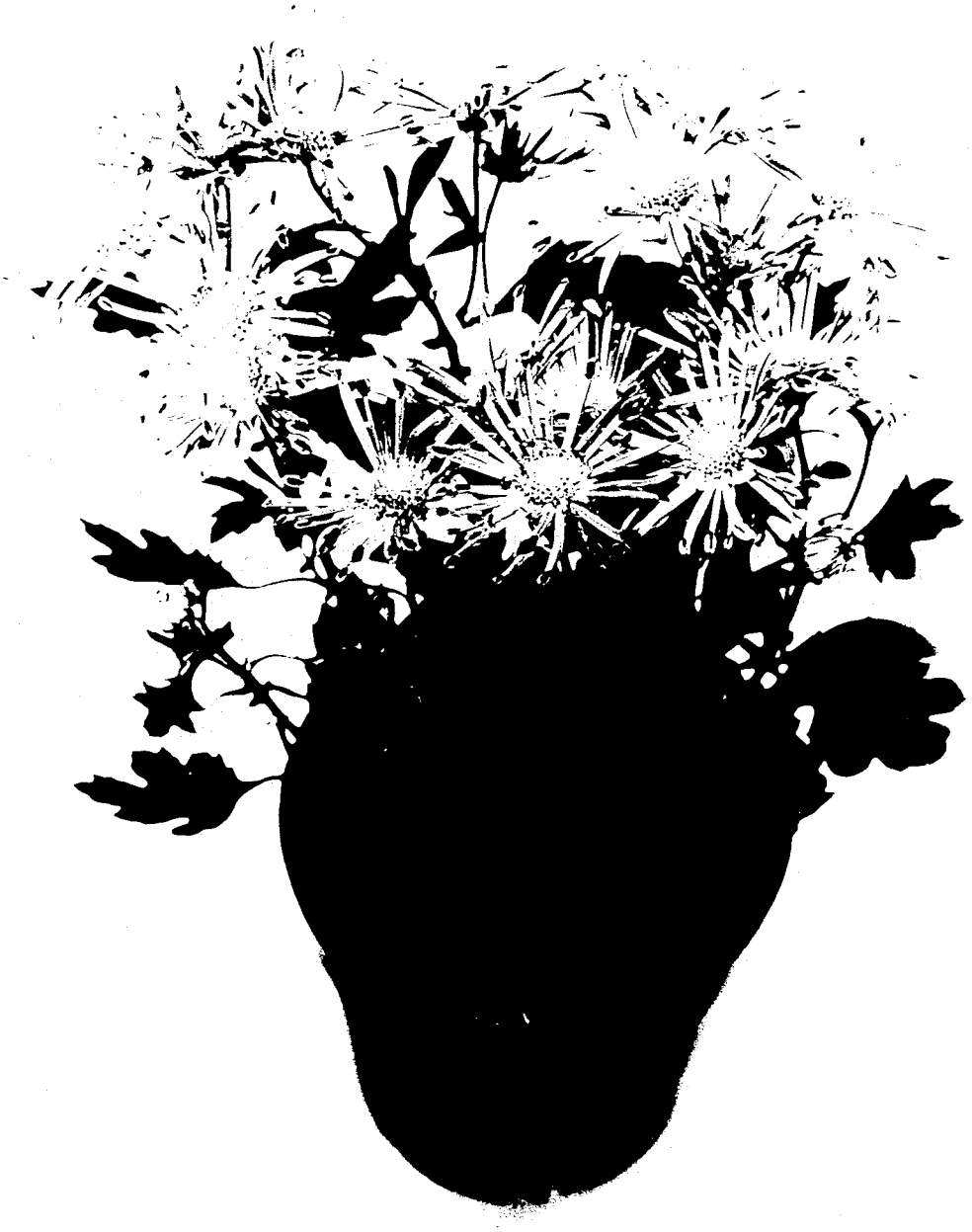

* * * * *